United States Patent

Hooven et al.

[11] Patent Number: 6,113,596
[45] Date of Patent: Sep. 5, 2000

[54] COMBINATION MONOPOLAR-BIPOLAR ELECTROSURGICAL INSTRUMENT SYSTEM, INSTRUMENT AND CABLE

[75] Inventors: Michael D. Hooven; Theodore A. Richardson, both of Cincinnati, Ohio

[73] Assignee: Enable Medical Corporation, West Chester, Ohio

[21] Appl. No.: 08/948,745

[22] Filed: Oct. 10, 1997

Related U.S. Application Data

[63] Continuation-in-part of application No. 08/774,771, Dec. 30, 1996, abandoned.

[51] Int. Cl.[7] ................................................... A61B 17/36
[52] U.S. Cl. ............................................................ 606/42
[58] Field of Search .............................. 606/41, 42, 45, 606/50, 34; 607/2

[56] References Cited

U.S. PATENT DOCUMENTS

| | | |
|---|---|---|
| 874,178 | 12/1907 | De Forest . |
| 3,089,496 | 5/1963 | Degelman . |
| 3,952,748 | 4/1976 | Kaliher et al. . |
| 4,041,952 | 8/1977 | Morrison, Jr. et al. . |
| 4,051,855 | 10/1977 | Schneiderman . |
| 4,071,028 | 1/1978 | Perkins . |
| 4,123,673 | 10/1978 | Gonser . |
| 4,171,700 | 10/1979 | Farin . |
| 4,184,492 | 1/1980 | Meinke et al. . |
| 4,244,371 | 1/1981 | Farin . |
| 4,311,144 | 1/1982 | Harada . |
| 4,331,149 | 5/1982 | Gonser . |
| 4,617,927 | 10/1986 | Manes . |
| 4,658,819 | 4/1987 | Harris et al. . |
| 4,708,137 | 11/1987 | Tsukagoshi . |
| 4,739,759 | 4/1988 | Rexroth et al. . |
| 4,860,745 | 8/1989 | Farin et al. . |
| 4,911,159 | 3/1990 | Johnson et al. . |
| 4,927,420 | 5/1990 | Newkirk et al. . |
| 4,931,047 | 6/1990 | Broadwin et al. . |
| 5,035,695 | 7/1991 | Weber, Jr. et al. . |
| 5,067,953 | 11/1991 | Feucht . |
| 5,080,660 | 1/1992 | Buelna . |
| 5,098,430 | 3/1992 | Fleenor . |
| 5,167,659 | 12/1992 | Ohtomo et al. . |
| 5,234,429 | 8/1993 | Goldhaber . |

(List continued on next page.)

FOREIGN PATENT DOCUMENTS

0717966A1  6/1996  European Pat. Off. .

Primary Examiner—Marvin M. Lateef
Assistant Examiner—Shawna J Shaw
Attorney, Agent, or Firm—Cook, Alex, McFarron, Manzo, Cummings & Mehler, Ltd.

[57] ABSTRACT

An electrosurgical instrument system including an RF energy source that has two bipolar terminals of opposite polarity and two monopolar terminals, one being active and the other being passive. Switches are provided for selectively energizing the bipolar terminals and the monopolar terminals. The system includes an electrosurgical instrument that has two tissue-contacting members and at least two electrodes. One electrode may be associated with each of the tissue-contacting members, or both electrodes may be associated with one of the tissue-contacting members. Two conductors are provided for connecting the two electrodes to the positive and negative bipolar terminals respectively. A third conductor is provided for connecting either of the electrodes or one of the tissue-contacting members to the active monopolar terminal. The system also includes a patient return electrode pad which is in electrical communication with the pass of monopolar terminal. Consequently, the instrument may be selectively used in the either the monopolar mode or the bipolar mode by engagement of the appropriate switch. In addition, an instrument for use in such a system as disclosed, which comprises any of a variety of bipolar electrosurgical instruments, including scissors, graspers, and forceps. A separate conductor assembly is also disclosed. In a further embodiment, switching circuitry is disclosed that senses bipolar or monopolar current and automatically connects the electrosurgical instrument to contact with the leads for the sensed current.

46 Claims, 10 Drawing Sheets

U.S. PATENT DOCUMENTS

| | | |
|---|---|---|
| 5,244,462 | 9/1993 | Delahuerga . |
| 5,277,201 | 1/1994 | Stern . |
| 5,324,289 | 6/1994 | Eggers . |
| 5,342,359 | 8/1994 | Rydell . |
| 5,352,222 | 10/1994 | Rydell . |
| 5,366,476 | 11/1994 | Noda . |
| 5,382,247 | 1/1995 | Cimino et al. . |
| 5,383,876 | 1/1995 | Nardella . |
| 5,403,312 | 4/1995 | Yates et al. . |
| 5,415,656 | 5/1995 | Tihon et al. . |
| 5,443,463 | 8/1995 | Stern et al. . |
| 5,456,684 | 10/1995 | Schmidt et al. . |
| 5,472,442 | 12/1995 | Klicek . |
| 5,496,312 | 3/1996 | Klicek . |
| 5,562,503 | 10/1996 | Ellman et al. . |
| 5,573,424 | 11/1996 | Poppe . |
| 5,954,719 | 9/1999 | Chen et al. .................. 606/42 |

MONOPOLAR COAG FINGER SWITCH

FIG. 15B

MONOPOLAR CUT/COAG FINGER SWITCH

COMBINATION MONOPOLAR-BIPOLAR ELECTROSURGICAL INSTRUMENT SYSTEM, INSTRUMENT AND CABLE

CROSS REFERENCE TO RELATED APPLICATION

This application is a continuation-in-part of application Ser. No. 08/774,771, filed Dec. 30, 1996 now abandoned.

This application relates to an electrosurgical system, including an instrument and associated cable, that can be used in either monopolar or bipolar mode according to the preferences of the physician using the system.

BACKGROUND

Electrosurgical techniques have come into widespread and accepted use in both open and minimally invasive surgical procedures for cutting or coagulating tissue and controlling bleeding or fluid loss through cauterization.

Presently, electrosurgical instruments are of two general types: monopolar and bipolar. A monopolar electrosurgical system includes an instrument comprising an electrode that is conductively connected to the active terminal of a monopolar RF generator. A passive or return electrode in the form of a pad is conductively connected to the generator's return terminal. The pad is placed beneath the patient adjacent the site where the electrosurgical procedure is being performed. In use, current passes from the generator's active terminal to the electrosurgical instrument, through the patient's body to the pad and back to the return terminal of the generator. Monopolar electrosurgical instruments are used primarily for electrosurgical cutting of tissue (as opposed to the mechanical cutting of tissue) and provide for a generally wide-reaching coagulation.

In contrast, bipolar electrosurgical systems include instruments which have both a positive and negative electrodes on the instrument itself, which electrodes are connected to the positive and negative terminals of a bipolar RF generator. Bipolar electrosurgical scissors are disclosed in the co-pending application Ser. No. 399,421, filed Mar. 7, 1995 and Ser. No. 593,148, filed Feb. 21, 1996. In the instruments disclosed in these applications, each blade of the scissors includes both a positive and negative electrode separated by an insulation layer to prevent shorting between the two electrodes. Other bipolar electrosurgical scissors are shown in Rydell U.S. Pat. No. 5,352,222, Eggers U.S. Pat. No. 5,324,289, and EPO Published Application 717 966 A1. Bipolar electrosurgical instruments generally provide the surgeon with greater control of the path of the RF energy through the patient, as the RF energy generally passes only through the tissue located between the electrodes of opposite polarity on the instrument, and not otherwise through the patient's body. Thus, bipolar electrosurgical instruments may provide for a more refined surgical technique and more predictable current flow.

There are often situations during the course of a single surgical procedure in which the use of both monopolar and bipolar electrosurgical instruments has its advantages. Consequently, RF generators are available that provide for generation of both monopolar and bipolar RF energy, for example, the Valley Lab Force 2 RF generator. This combination generator includes two bipolar terminals and active and passive monopolar terminals, and it is contemplated that two different types of instruments, monopolar, and bipolar, can be connected to the generator simultaneously. However, such a system requires the surgeon to have both a monopolar and bipolar instrument at hand, rather from a single instrument that performs both monopolar and bipolar procedures.

More recently, an adapter for connecting a bipolar instrument to the monopolar active output of an RF generator has been proposed, see U.S. Pat. No. 5,573,424 to Poppe. While the same instrument can be used for both monopolar and bipolar electrosurgical surgery using this adapter, the Poppe device still requires that the instrument be unplugged and the adapter removed or attached before switching the instrument between the bipolar terminals and the monopolar active terminal of an RF generator.

Accordingly, it is an object of the present invention to provide an electrosurgical system, instrument and cable that permits both bipolar electrosurgical techniques and monopolar electrosurgical techniques to be performed with the same instrument without having to disconnect the instrument from the RF generator. More specifically, it is an object of the present invention to provide an electrosurgical system, instrument and cable in which the instrument may be simultaneously connected to both the active terminal of a monopolar RF generator and to the positive and negative terminals of a bipolar RF generator, so that the instrument can be used as either a monopolar or bipolar instrument merely by use of a switch associated with either the RF generator or the instrument.

It is a further object of the present invention to provide an electrosurgical instrument that can be used as both a bipolar instrument and a monopolar instrument without having to disconnect the instrument from the RF generator, merely by use of a switch associated with any of the RF generator, cable, adapter, or instrument.

It is an additional object of the present invention to provide a conductor cable for a bipolar instrument that allows the instrument to be used as both a monopolar and bipolar instrument.

It is a further object to provide an electrosurgical system and cable that automatically switches the instrument into contact with the monopolar active or bipolar terminals of an RF generator based upon the sensing of either monopolar or bipolar current from the RF generator.

SUMMARY OF THE INVENTION

In accordance with the present invention an electrosurgical instrument system is provided including an RF energy source that has two bipolar terminals of opposite polarity and two monopolar terminals, one being active and the other being passive. Switches are provided for selectively energizing the bipolar terminals and the monopolar terminals. The system includes an electrosurgical instrument that has two tissue-contacting members and at least two electrodes. One electrode may be associated with each of the tissue-contacting members, or both electrodes may be associated with one of the tissue contacting members. Two conductors are provided for connecting the two electrodes to the positive and negative bipolar terminals, respectively. A third conductor is provided for connecting either of the electrodes or one of tissue-contacting members to the active monopolar terminal. The system also includes a patient return electrode pad that is in electrical communication with the passive monopolar terminal. Consequently, the instrument may be selectively used in either the monopolar mode or the bipolar mode by engagement of the appropriate switch.

In accordance with another aspect of the invention an electrosurgical instrument is provided including two tissue-contacting members and at least two electrodes, with one electrode associated with each of the tissue contacting members, or both electrodes associated with one of the tissue-contacting members. Each of the two electrodes is connected to a conductor adapted to receive RF energy from one of the bipolar terminals of a generator so that the electrodes are of the opposite polarity. A third conductor is provided for simultaneously connecting either of the electrodes on one of the tissue-contacting members to the active monopolar terminal.

The system and instrument may each comprise any of a variety of bipolar electrosurgical instruments, including scissors, graspers, and forceps. In addition, the tissue-contacting members may each support two electrodes that, when connected to the bipolar terminals of the RF generator, are of opposite polarity.

The invention also includes a conductor assembly for the simultaneous connection of a bipolar electrosurgical instrument to the monopolar active and bipolar terminals of a combination RF generator.

In accordance with a further aspect of the invention, the conductor is an assembly comprising a controller that is operable to switch the output that connects the electrosurgical instrument into communication with either the monopolar active or bipolar terminals of the RF generator, depending upon detecting the activation of either the monopolar or bipolar energy. In one embodiment, the output of the controller is normally connected to the monopolar active terminal and, upon sensing bipolar energy the output of the controller is switched into contact with the bipolar terminals. In a second embodiment, the output of the controller is normally connected to the bipolar output terminals and, upon sensing monopolar current, the output of the controller is switched into contact with the monopolar active terminal. Specific circuitry for these two embodiments of the controller is disclosed. In each embodiment, the output of the adaptor is disconnected from communication with the monopolar active terminal before being connected to the bipolar output terminal, and vice versa. The controller may also be either separate from the RF generator or contained within the RF generator housing itself.

BRIEF DESCRIPTION OF THE DRAWINGS

FIG. 9b is a diagram illustrating the various conductors associated with the scissor blades of FIG. 9a.

DETAILED DESCRIPTION

Figure 1A:
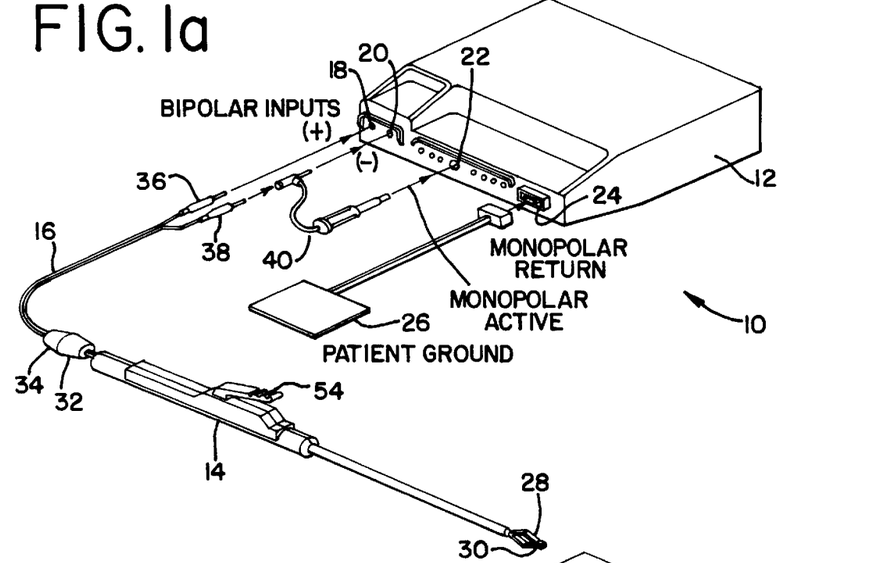
FIG. 1a is a diagrammatic representation of an electrosurgical instrument system embodying the present invention.

Turning to FIG. 1a, there is seen an electrosurgical instrument system, generally designated 10, embodying the present invention. The system 10 includes a unitary monopolar/bipolar RF energy generator 12, a hand-held electrosurgical instrument 14, and a cable, generally at 16, that simultaneously connects the instrument 14 to the monopolar and bipolar outputs of the generator 12.

The RF energy generator 12 includes a front panel that has plug clip receptacles 18, 20 for the positive and negative bipolar outputs, a plug clip receptacle 22 for the monopolar active terminal 22, and a pin connector 24 for the monopolar return terminal. A typical patient ground pad 26 is connected to the monopolar return terminal 24, as is well-known in the art. Switching of the generator 12 between bipolar and monopolar RF generation may be accomplished by, e.g., foot pedals (not shown) so that such switching may be done conveniently by the surgeon during a procedure without having to set down the instrument 14.

The electrosurgical instrument 14 can be any of a number of bipolar electrosurgical scissors, graspers or forceps, such as those described in the applicant's co-pending applications, Ser. No. 399,421, filed Mar. 7, 1995, and Ser. No. 593,148, filed Feb. 21, 1996, as well as U.S. Pat. Nos. 5,324,289, 5,342,359, 5,352,222 and 5,403,312, and EPO published application 717,966 A1, all of which are incorporated herein by reference.

The instrument 14 includes two generally opposed tissue-contacting members 28, 30 on which electrodes are supported in the manner set forth in any of the above-incorporated applications and patents. The instrument 14 includes a bipolar polarized, female connector 32 that connects to two conductors that extend through the instrument body to the electrodes supported by the tissue-contacting members 28, 30. The cable 16 is a standard two conductor cable having conductors 37, 39 terminating at one end in a polarized male bipolar connector 34 for mating with the connector 32 on the instrument. At their other end, the conductors 37, 39 terminate in two clip connectors 36, 38 that can be received in the bipolar terminals 18, 20 of the generator 12.

In order to simultaneously conductively connect one of the electrodes of the bipolar instrument 14 to the monopolar active terminal 22 of the generator 12, a third conductor, generally indicated by 40, is provided to connect one of the two bipolar connectors 36, 38 simultaneously to the monopolar active terminal 22 and one of the bipolar terminals 18, 20.

Figure 2:
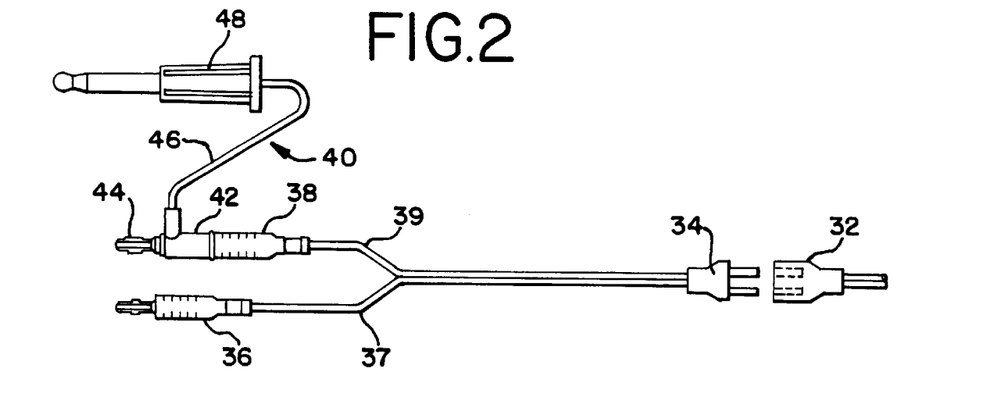
FIG. 2 is a conductor cable shown in FIG. 1a for simultaneously connecting a bipolar electrosurgical instrument to the terminals of a bipolar and monopolar RF generator.

As best seen in FIG. 2, the conductor 40 includes an adaptor clip 42 that simultaneously receives the pin portion of the clip connector 38 and includes a pin 44 that can be received by one of the bipolar terminals of the generator. An insulated conductor 46 connects the adapter clip 42 to a plug connector 48 sized to be received in the monopolar active terminal 22 of the generator 12. Thus, the third conductor 40 provides simultaneous connection of the conductor 39 to either of the bipolar terminals 18, 20 and the monopolar active terminal 22 of the RF generator 12. Consequently, in the illustrated system, the same electrode that receives its bipolar current through the conductor becomes the monopolar active terminal when the instrument 14 is used in the monopolar mode.

Figure 1B:
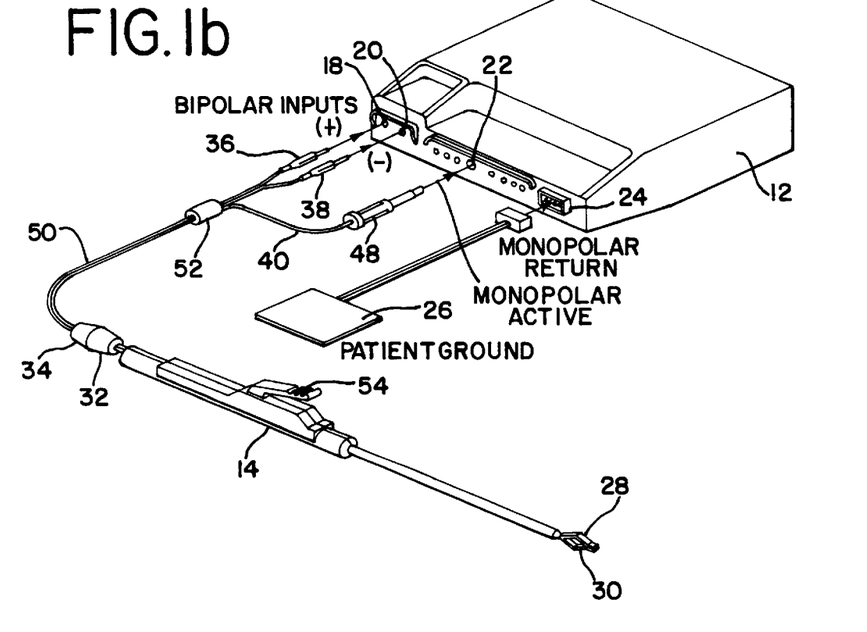
FIG. 1b is a diagrammatic representation of an alternate embodiment of an electrosurgical instrument system incorporating the present invention.
Figures 3, 3A:
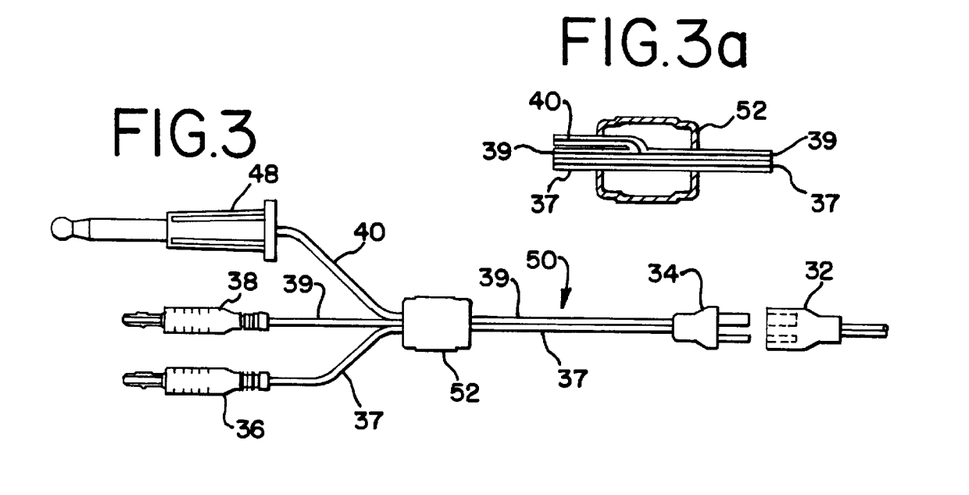
FIG. 3 is a conductor cable as shown in FIG. 1b.
FIG. 3a is an enlarged cross-sectional view of a housing utilized in the conductor of FIG. 3.

FIG. 1b shows an alternate embodiment of the inventive system that differs from the embodiment in FIG. 1a in that the conductors 37, 39 and 40 connecting the instrument 14 to the generator 12 are combined into a unitary conductor, generally at 50. As best seen in FIG. 3, the cable 50 includes a polarized male bipolar connector 34 for mating with the female bipolar connector 32 on the instrument 14. Clip connectors 36 and 38 are provided for mating with the bipolar terminals 18, 20 of the generator 12 and a plug connector 48 is provided for mating with the monopolar active terminal 22 of the generator 12. Like the cable of FIG. 2, the conductors 37, 39 extend from the clip connectors 36, 38 to the male connector 34. However, intermediate the clip connectors 36, 38 and the male plug 34, the conductor 40 ties into the conductor 39. The connection between the conductor 40 and conductor 39 is protected within a housing 52, shown in cross-section in FIG. 3a.

Figure 4:
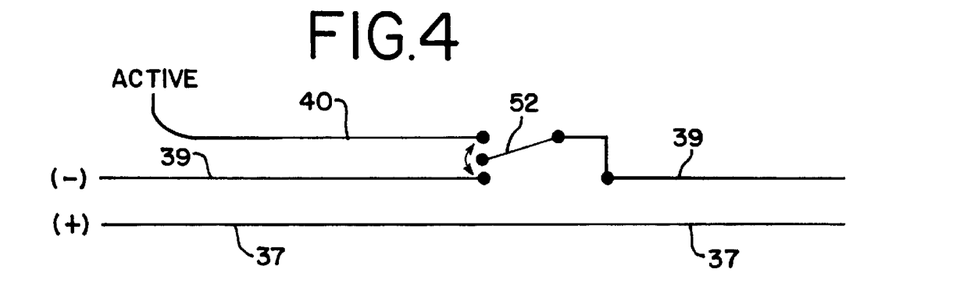
FIG. 4 is a switch circuit suitable for use in the system of FIGS. 1a or 1b.

The particular advantage of the embodiments shown in FIGS. 1a, 1b, 2, 3, and 3a is that they all permit use of bipolar electrosurgical instruments without any modification to the instrument itself. However, the cables 16 or 50 can be eliminated if the electrosurgical instrument is constructed so that each of the conductors 37, 39, and 40 leading from the bipolar terminals 18, 20 and the monopolar active terminal 22 extend all the way from the terminals to the instrument. In such an embodiment, the monopolar active conductor 40 can be selectively connected to the bipolar conductor 39 by means of, e.g., a switch 52 moveable between two positions. The switch 52 can be manipulated by a lever, such as lever 54, on the hand-held part of the instrument 14. The switch is shown schematically in FIG. 4.

In all of the embodiments thus far discussed, one of the bipolar electrodes on the instrument also serves as the monopolar active electrode. However, the present invention contemplates that a portion of the tissue engaging members 28, 30 other than the electrode can serve as the active electrode when the instrument is in the monopolar mode. Specifically, in several embodiments of bipolar electrosurgical instruments the tissue-contacting members 28, 30 are substantially more massive than the electrodes that are secured thereto. Thus, if these tissue-contacting members are conductive, they may be better suited to carry the larger currents associated with monopolar electrosurgery than are the electrodes that may be mounted thereon. Thus, in such embodiment, the conductor 40 connecting to the active monopolar terminal 22 of the generator 12 does not tie into one of the conductors 39, 37 leading the electrodes on the bipolar surgical instrument, but instead RF energy is conducted directly to one of the more massive tissue-contacting members.

To better illustrate the effect of the present invention on typical bipolar electrosurgical instruments, FIGS. 5a–9a are diagrammatic cross-sections of the blades of various bipolar electrosurgical scissors with the scissors in the bipolar mode. FIGS. 5b–8b, 5c–8c and 6d are diagrammatic cross-sectional views of the same scissor blades in the monopolar mode with the monopolar conductor 40 variously connected to the electrodes or to a body portion of the tissue-contacting member.

Figure 5A:
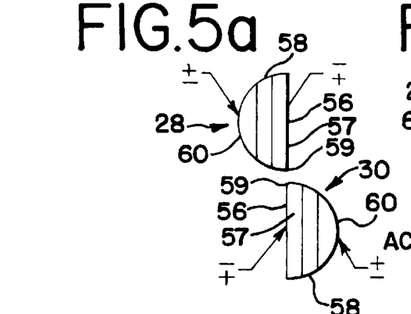
FIGS. 5a–c are cross-sectional views of a pair of bipolar electrosurgical scissor blades with two electrodes on each blade embodying the present invention, and indicating the polarity of the electrodes and blade members when in the bipolar mode (FIG. 5a) and the monopolar mode (FIGS. 5b–c).
Figures 5B, 5C:
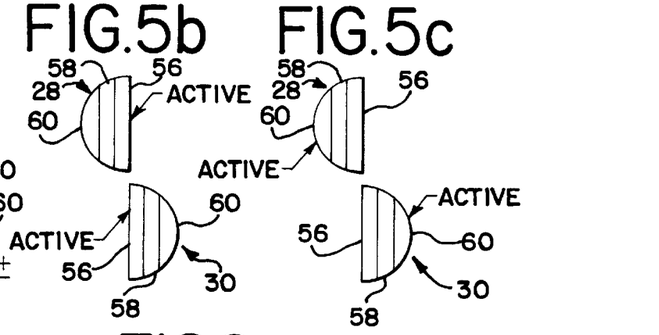

Turning now specifically to FIGS. 5a–5c there are seen two tissue-contacting members 28, 30 that comprise scissor blades. Each tissue-contacting member 28, 30 includes an inner electrode 56 that also comprises the shearing surface 57 and cutting edge 59 of the blade member. Spaced from the inner electrode 56 by an insulating layer 58 is an outer electrode 60. Thus, each blade member 28, 30 includes both a positive and a negative electrode when in the bipolar mode, with the shearing face 56 of each member 28, 30 being of the same polarity, either positive or negative (as indicated by ⁻), with the outer electrode 60 of each member 28, 30 being of the same polarity, but opposite to that of the inner electrode 56 (as indicated by ±). Such a bipolar scissors construction is more specifically shown and described in the two co-pending applications cited above. When such scissors are in the monopolar mode, either the inner electrodes 56 can be the active electrode (as shown in FIG. 5b) or the outer electrode 60 of each blade member 28, 30 will be conductively connected to the monopolar active terminal of the generator (as shown in FIG. 5c).

Figure 6A:
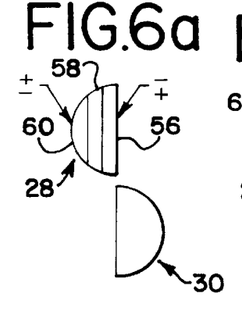
FIGS. 6a–d are cross-sectional views of a pair of bipolar electrosurgical scissor blades with two electrodes on one blade member and the other blade member being a simple blade, and indicating the polarity of the electrodes and blade member when in the bipolar mode (FIG. 6a) and the monopolar mode (FIGS. 6b–d).
Figures 6B, 6C, 6D:
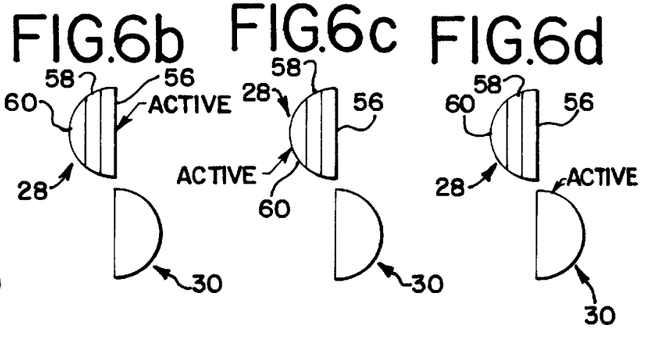

The scissor blades depicted in FIGS. 6a–d include one composite blade 28 which has both the bipolar electrodes 56, 60 separated by an insulating layer 58, with the second blade member 30 being a simple conductive member having a generally uniform metallic construction. Such a scissors is shown and described in the EPO published application 717,966 A1 referred to above. Thus, when the instrument of 6a is in the bipolar mode, the electrodes 56, 60 are of opposite polarity, as indicated by the ∓ for electrode 56, and the ± for electrode 60. In the monopolar mode, one of the electrodes 56, 60 can be in electrical communication with the third conductor 40 for connection to the monopolar active terminal of the RF energy source so as to become the monopolar active electrode (FIGS. 6b, 6c) or the blade member 30 can be in electrical communication with the third conductor 40 for connecting to the monopolar active terminal so that it becomes the monopolar active electrode (FIG. 6d).

Figures 7A, 7B:
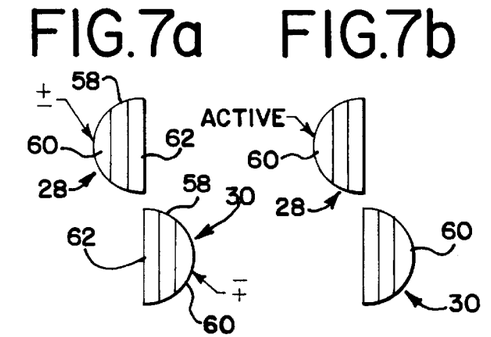
FIGS. 7a–c are cross-sectional views of a pair of bipolar electrosurgical scissor blades with one electrode on each blade, and indicating the polarity of the electrodes and blade members when in the bipolar mode (FIG. 7a) and the monopolar mode (FIGS. 7b–d).
Figure 7C:
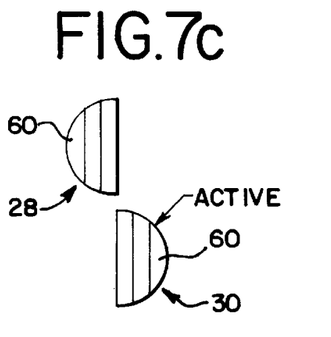

The tissue contacting members 28, 30 shown in FIGS. 7a–c are similar to those disclosed in U.S. Pat. No. 5,352,222 in that each tissue contacting member 28, 30 carries only one electrode 60 on the outer surface thereof, the electrodes being of opposite polarity when in the bipolar mode (FIG. 7a). Specifically, each tissue-contacting member comprises a laminated assembly of a metal shearing surface 62, with the electrode 60 being part of a metal support separated from the shearing surface 62 by an intermediate insulative layer 58. Such a scissors would employ a conductor 40 that connects into one of the bipolar conductors 37, 39 (as shown, e.g., in FIGS. 1a, 1b, 2 and 3) so that when in the monopolar mode, either the electrode 60 on blade member 28 becomes the active electrode (FIG. 7b) or the electrode 60 on blade member 30 becomes the active electrode (FIG. 7c).

Figures 8A, 8B:
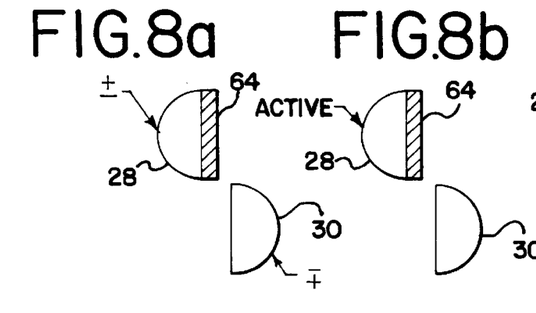
FIGS. 8a–c show an alternate construction of the scissor blades of FIGS. 7a–c.
Figure 8C:
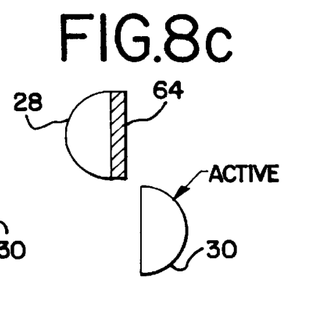

A still further embodiment of bipolar scissors with which the present invention can be advantageously utilized is shown in FIGS. 8a–c. The tissue-contacting members 28, 30 are similar to of those described and shown in U.S. Pat. No. 5,324,289, in which each tissue-contacting member comprises a conductive material, and the shearing surface of one of the blade members (shown as member 28) includes an electrically insulative layer 64 so that the blade members 28, 30 do not short in the bipolar mode due to their shearing surfaces being in face-to-face contact. Consequently, when in the bipolar mode (FIG. 8a) each tissue-contacting member 28, 30 comprises the electrode, with each electrode being of the opposite polarity. When the instrument is used in the monopolar mode, either tissue-contacting member 28 will be the monopolar active electrode (FIG. 8b) or tissue-contacting member 30 will be the active monopolar electrode (FIG. 8c).

Figure 9A:
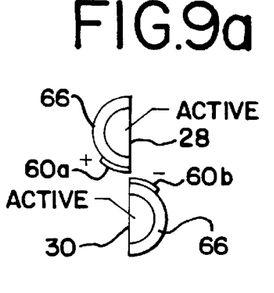
FIGS. 9a, c and d show alternate constructions of the scissor blades of FIGS. 8a–c.
Figure 9B:
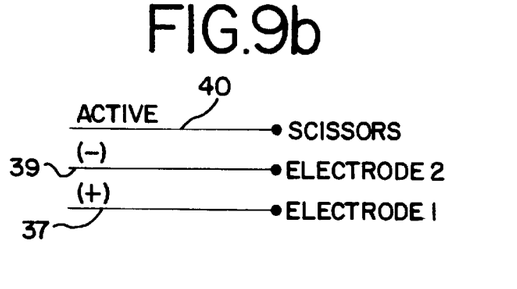
Figure 9C:
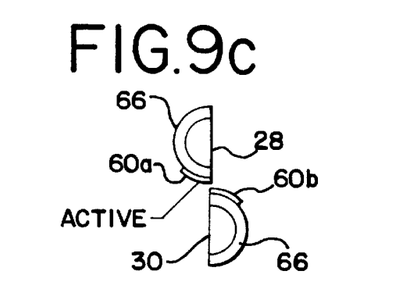
Figure 9D:
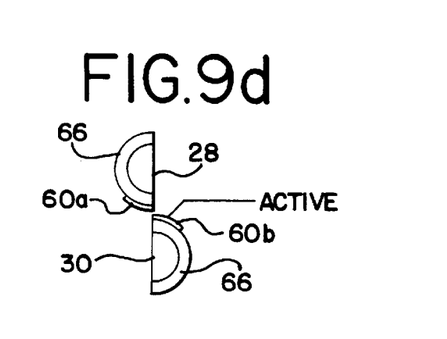

FIG. 9a shows a variation of the tissue-contacting members of FIGS. 8a–8c in which the tissue-contacting members 28, 30 each include an insulative layer 66 on the outer surface thereof with a separate electrode 60a, 60b of opposite polarity supported by the insulative layer. Thus, in the bipolar mode, the tissue-contacting members are passive electrical conductors and do not carry current. However, the conductor 40 (FIG. 9b) connects one of the tissue-contacting members 28, 30 to the active terminal. Because of the face-to-face contact of the shearing surfaces of the members 28, 30, when the device is switched to the monopolar mode, both of the support members 28, 30 will become the active monopolar terminal. Alternatively, as shown in FIGS. 9c and 9d, just one of the separate electrodes 60a (FIG. 9c) or 60b (FIG. 9d) can be connected to the active terminal.

Figure 10A:
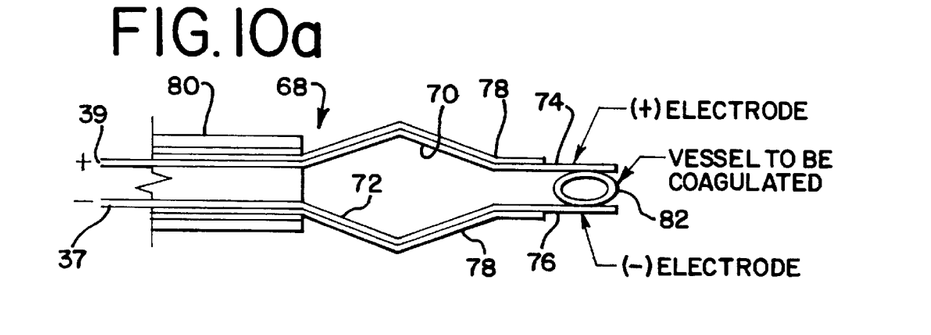
FIGS. 10a–b show a pair of bipolar electrosurgical forceps with one electrode on each engageable tip, and indicating the polarity of the electrodes when in the bipolar mode (FIG. 10a) and the monopolar mode (FIG. 10b).
Figure 10B:
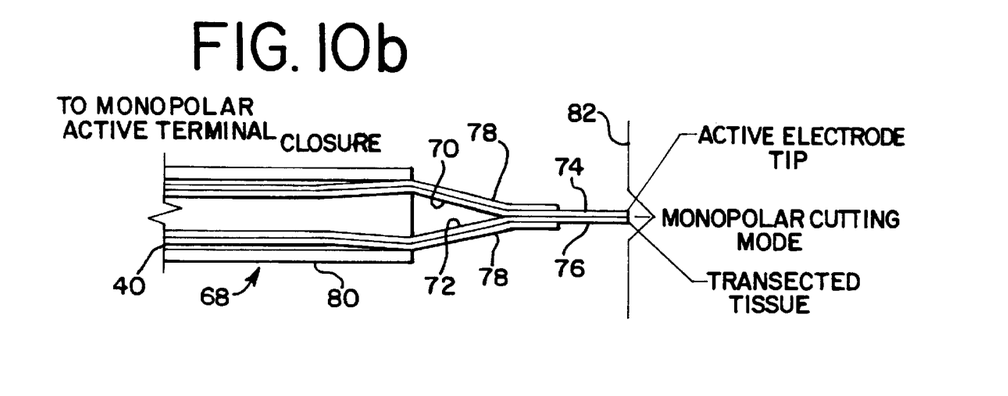

While the combination monopolar/bipolar instrument has been described thus far in the context of electrosurgical scissors, other bipolar instruments, such as forceps and graspers (such as those shown in the above-identified U.S. Pat. Nos. 5,342,359 and 5,403,312), may also advantageously use the present invention. Turning to FIGS. 10a–b, there is seen a forceps embodying the present invention in which the forceps are being used in the bipolar mode to coagulate a vessel (FIG. 10a), and in the monopolar mode to transect tissue (FIG. 10b). The forceps are standard Kleppinger bipolar forceps well known in the art that are closed and opened by a switch on the instrument that actuates a slidable sleeve to provide a camming force on the arms of the forceps. Specifically, the forceps 68 includes two arms 70, 72 made of, for example, spring steel, that terminate in tips 74, 76. The arms are connected by conductors 37, 39 to the positive and negative bipolar terminals of a generator. The arms 70, 72 are also covered with an insulating material 78 that terminates short of the tips 74, 76. The forceps 68 extend out from a retracted slidable sleeve 80 when the forceps are used in their conventional bipolar mode. In use, the tips 74, 76 of the forceps are used to engage, for example, a vessel 82 and bipolar RF energy is applied to the arms 70, 72 to coagulate the vessel.

One of the arms of the forceps (as shown, arm 72) is also connected to the monopolar active terminal in the manner described above. When the forceps 68 are used in the monopolar mode, the slidable sleeve 80 is advanced toward the tips 74, 76 of the forceps, creating a camming action on the arms 70, 72 to force the tips to contact each other and provide, in essence, a single electrode. When monopolar RF energy is applied to the instrument, the tips 74, 76 act as monopolar cutting tool for transecting tissue, as shown in FIG. 10c. The instrument can be constructed so that monopolar energy can be applied to the tips 74, 76 only when the sleeve is slid forward to bring the tips into contact, thus making inadvertent activation of the monopolar energy less likely.

In keeping with a further aspect of the present invention, the conductors connecting the RF energy source to the electrosurgical instrument include a controller having a bipolar input for connecting to the conductors leading to the bipolar outputs, a monopolar input for connecting to the conductor leading to the monopolar active terminal of the RF generator, and an output to connect to the electrodes of the electrosurgical instrument. The controller is operable to switch the output of the controller into communication with either the monopolar conductor or the bipolar conductor upon the detection of monopolar or bipolar output current. In one embodiment, the controller is operable to automatically connect the two bipolar leads to the output of the controller upon the activation of bipolar energy from the RF generator and connects the monopolar active lead to the output of the controller when bipolar energy is deactivated. In a second embodiment, the controller is operable to automatically connect the monopolar active lead to the output of the controller upon the activation of monopolar energy from the RF generator and connect the bipolar leads to the output of the controller upon deactivation of monopolar energy.

Figure 11:
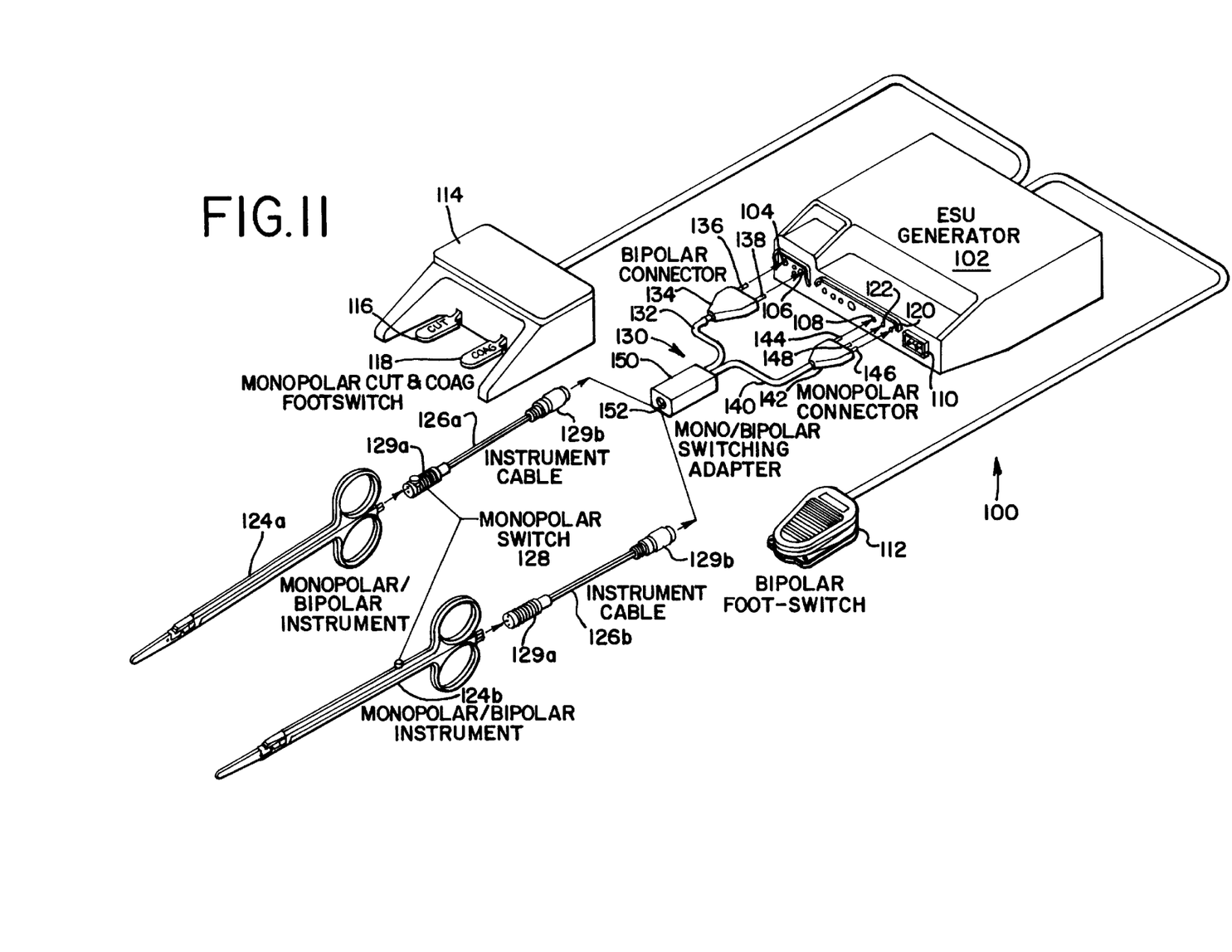
FIG. 11 is a diagrammatic perspective view of an electrosurgical instrument system in which the conductor cable includes a controller that automatically switches the output of the conductor to contact with the monopolar active or bipolar terminals upon detecting the activation of either monopolar or bipolar energy.

Turning now to FIG. 11, there is seen an electrosurgical instrument system, generally designated 100, including the automatic controller described above. The system 100 includes an RF energy generator 102 similar to that described above. The face of the generator 102 includes bipolar outputs 104, 106 of opposite polarity, a monopolar active output 108, and a pin connector 110 for the monopolar return, to which a patient ground pad 111 (seen in FIG. 12) is connected.

Bipolar output current is activated by depressing a foot switch or pedal 112, the generation of bipolar energy stopping when the foot pedal is released. Similarly, monopolar current is activated by depressing the monopolar foot switch 114, monopolar energy stopping when the foot switch is released. The monopolar foot switch 114 includes two pedals. Pedal 116 activates monopolar cut current, while pedal 118 activates monopolar coagulating current. Alternatively, the monopolar current can be activated by a switch on the instrument or instrument cable, which is described in greater detail below. When the controller for the monopolar current is on the instrument or instrument cable, the control is connected to a cut current controller output 120 and a coagulating current control output 122, both of which are on the face of the generator 102.

The system 100 includes an electrosurgical instrument, identified as either 124a or 124b and having at least two electrodes associated therewith, and a corresponding instrument cable 126a or 126b. As illustrated, the instruments 124a and 124b are scissors. However, the instrument could equally well be any other instrument, such as a graspers or forceps, having at least two electrodes associated therewith. Instrument 124a and cable 126a are interchangeable with instrument 124b and cable 126b.

The cables 126a and 126b each include two conductive leads 127a, 127b (FIG. 12)—one for each of the electrodes on the instrument—that extend between a female pin connector 129a for connecting to the instrument 124a or 124b, and a male connector 129b for connecting to a monopolar/bipolar adapter, such as that shown in FIGS. 2 and 3 or, preferably, like the adapter described below. In the case of instrument 124a and cable 126a, a monopolar current control switch 128 is carried by the female pin connector 129 on the instrument cable 126a. In instrument 124b and cable 126b, a monopolar current control switch 128 is located on the instrument 124b.

In keeping with another aspect of the invention, a monopolar/bipolar automatic switching adaptor, generally designated by 130, is provided to connect the instrument and instrument cable 124/126 to the RF energy generator 102. The adaptor 130 includes a bipolar input cable or conductor 132 including a connector 134 having contact pins 136 and 138 for connecting to the bipolar outputs 104, 106 of the RF generator 102. The adaptor 130 also includes a monopolar input cable or conductor 140 that includes a three pin connector 142 with pins 144, 146, 148 for connecting to the monopolar active output 108, the cut current control output 120, and the coagulating current control output 122, respectively.

As illustrated, the adaptor 130 includes a central housing 150 that encases the controller or switching circuitry (described below) and includes a cable receptacle 152 for mating with the proximal connector on the instrument cable 126.

Figure 12:
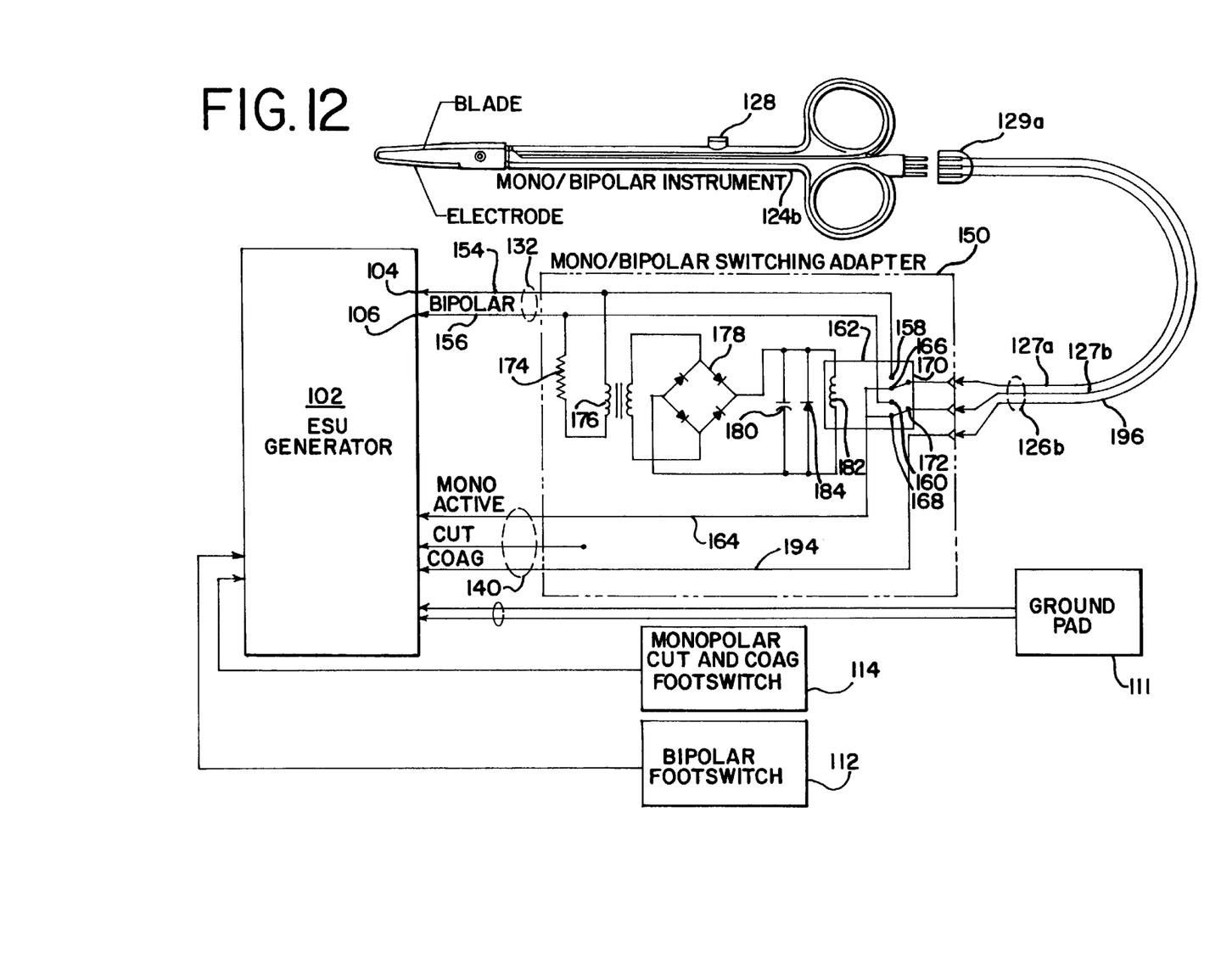
FIG. 12 is a diagrammatic representation of the electrosurgical instrument system of FIG. 11, including a switching circuit that is activated by bipolar output current.

Turning now to FIG. 12, there is seen a schematic representation of the electrosurgical instrument system 100, including a circuit diagram for a controller contained in housing 150 for the adaptor. As illustrated in FIG. 12, the adaptor normally connects the electrosurgical instrument 124b and instrument cable 126b to the monopolar active output 108 of the generator 102. Upon sensing bipolar energy, the controller switches the output 152 of the adaptor to contact with the bipolar outputs 104, 106 of the generator 102.

Specifically, the bipolar conductor 132 includes conductive leads 154, 156 that connect to the bipolar outputs 104, 106 of the generator 102 through the contact pins 136, 138. The bipolar conductive leads 154, 156 each terminate in a normally open contact 158, 160 of a double pole, double throw relay, generally indicated by 162. The monopolar input cable or conductor 140 includes a monopolar conductive lead 164 that is connected to the monopolar active terminal or output 108 of the generator 102 through contact pin 144. As illustrated, the monopolar conductive lead 164 terminates in the relay 162 with two normally closed contacts 166, 168. The output 152 of the adaptor is connected to the relay 162 and terminates within the relay 162 with contacts 170, 172. When the cable 126a or 126b is connected to the adapter 130, the contacts 170, 172 are conductively connected to the two conductive leads 127a, 127b that, in turn, connect to the two electrodes carried by the instrument 124a or 124b.

The relay 162 switches the contacts 170, 172 into contact with the bipolar contacts 158, 160 (and out of contact with monopolar contacts 166, 168), upon the sensing of bipolar output current by the controller. Thus, bipolar energy output current is transmitted to the electrodes carried by the instrument 124a or 124b. Conversely, when bipolar output current is no longer sensed by the controller, the contacts 170, 172 are switched back into contact with the monopolar contacts 166, 168. Thus, monopolar active energy, when activated, is transmitted to the electrodes carried by the instrument 124a or 124b. As can be readily appreciated, the relay 162 disconnects the contacts 170, 172 from the monopolar contacts 166, 168 before connecting with the bipolar contacts 158, 160, thus preventing any bipolar current from possibly being conducted back to the generator through the monopolar input. Similarly, the contacts 170, 172 are disconnected from the bipolar contacts 158, 160, before connecting to the monopolar contacts 166, 168, preventing any monopolar current from being conducted back to the bipolar output.

To automatically switch the relay between the normally closed contacts 166, 168 and the normally open contacts 158, 160, the bipolar leads 154, 156 are connected across a resistor 174 and a step-down transformer 176, the output of which is a reduced AC voltage. The controller includes a diode rectifier bridge 178, which rectifies the output of the transformer 176 to DC. The DC voltage is then filtered by a capacitor 180, and its output is used to actuate the relay 162 by means of a coil 182. The contacts 170, 172 of the relay 162 are connected to the instrument 124 via the cable 126 to connect to the two electrodes on the instrument. A diode 184 is connected in parallel with the coil 182 to dissipate current caused by de-energizing the relay 162.

Figure 13:
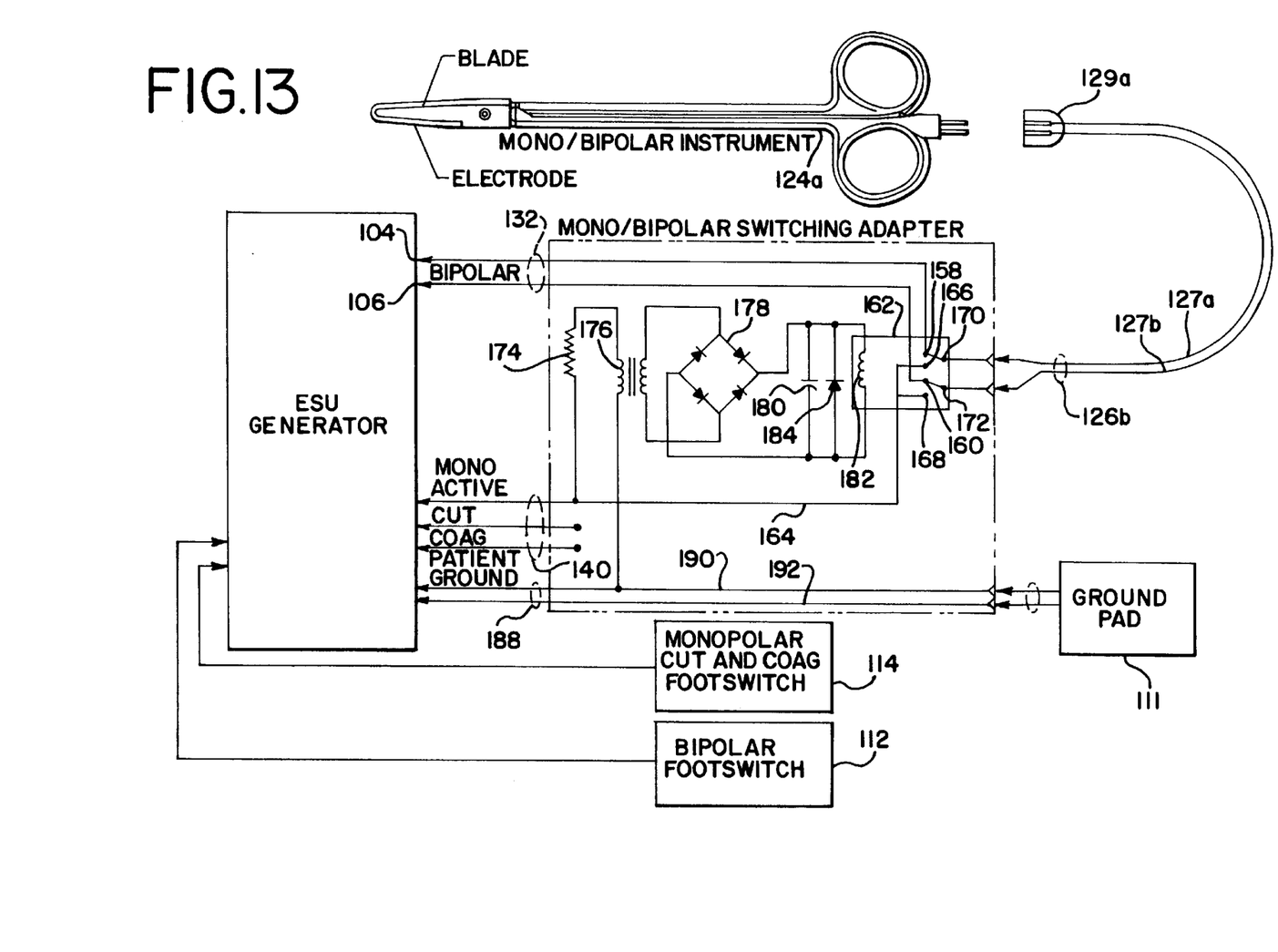
FIG. 13 is a diagrammatic representation of the electrosurgical instrument system of FIG. 11, including a switching circuit that is activated by monopolar output current.

In an alternate configuration of the automatic switching adaptor, monopolar energy is used to actuate the relay. Turning to FIG. 13, a schematic representation of such an electrosurgical instrument system 100 is shown. The system of FIG. 13 is similar to that of FIG. 12, except that the automatic switching adaptor 130 includes a monopolar return cable or conductor 186 that connects to the monopolar return pin connector 110 on the face of the generator 102. The adaptor 130 also includes a second cable receptacle or adaptor output 188 for receiving the pin connector from the patient ground pad 111. The monopolar return conductor 186 includes two monopolar return conductive leads 190, 192.

In contrast to the embodiment shown in FIG. 12, where the bipolar leads 154, 156 are connected across a resistor 174 and step-down transformer 176, the monopolar active conductive lead 164 and one of the monopolar return conductive leads 190 or 192 (shown as connected to conductive lead 190) are connected across the resistor 174 and step-down transformer 176. In addition, in the relay 162 of FIG. 13, contacts 158, 160, which are connected to the bipolar conductive leads 154, 156, are normally closed. Consequently, when monopolar current is activated in the system 100 of FIG. 13, monopolar current flows through resistor 174 and step-down transformer 176 to the monopolar return conductive lead 190 to activate the relay and open the bipolar contacts 158, 160 and close the monopolar contacts 166, 168 so that monopolar current flows to the adaptor output 152. The other components of the circuitry of the adaptor in FIG. 13 is identical to that in FIG. 12.

While the adaptor can be constructed so that it is activated by either bipolar or monopolar energy, there are certain advantages to using bipolar energy. Specifically, because the bipolar energy used for electrosurgery is of a much lower voltage than that of the monopolar energy used, the controller can use a less-expensive relay, as the contacts of the relay will not have to withstand the high monopolar voltages.

Figure 14:
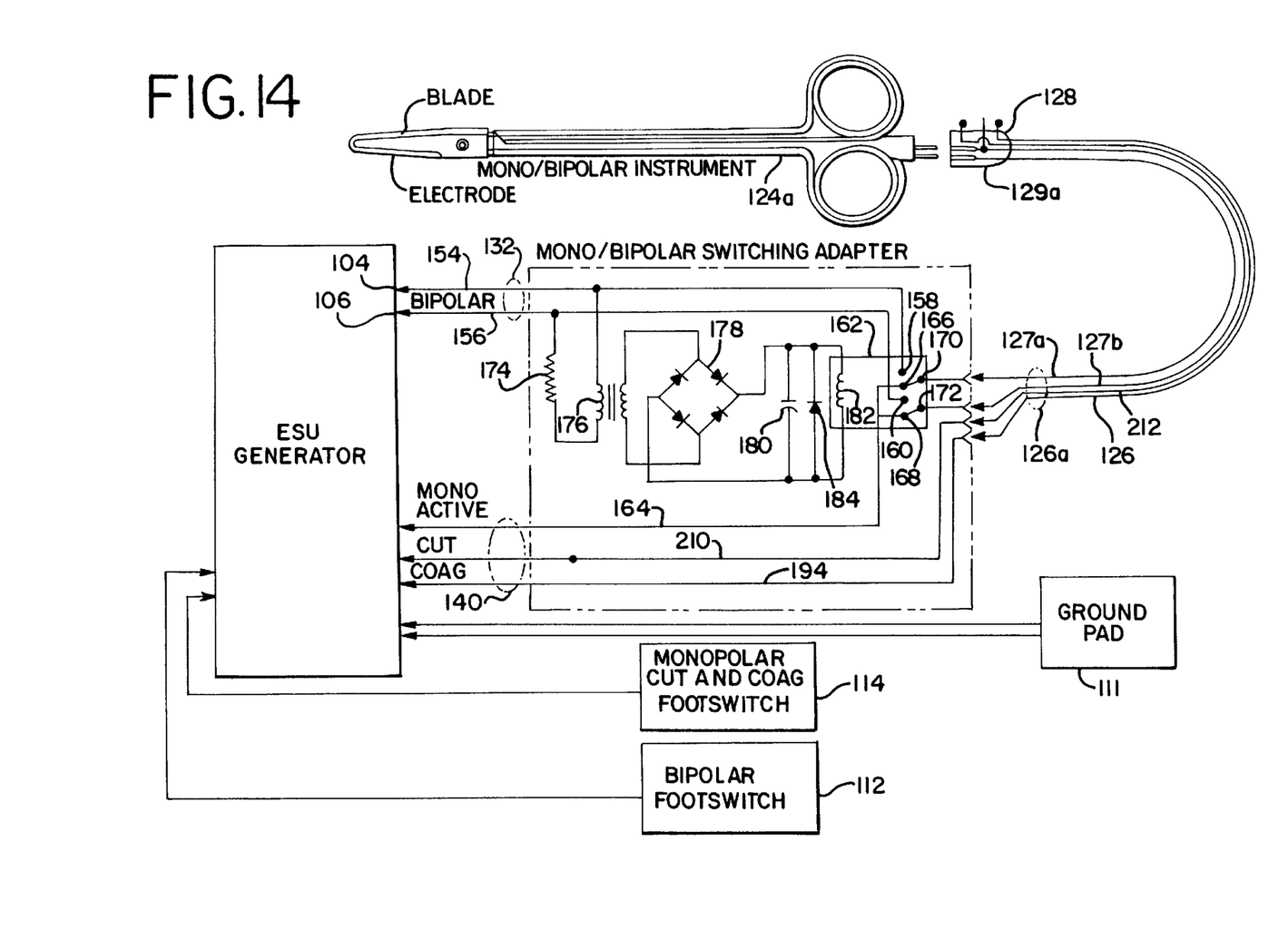
FIG. 14 is a diagrammatic representation of an alternative embodiment of the electrosurgical instrument system of FIG. 12.

As discussed above, monopolar current can be activated in the illustrated systems through use of the monopolar foot switch 114 (as illustrated in each of FIGS. 11–14), or additionally by a finger switch located either on the instrument 124b (the system of FIG. 12) or on the instrument cable 126a (the system of FIG. 14).

With reference FIG. 12, the instrument 124b incorporates a finger switch 128 which is operable to activate monopolar coagulating current. To this end, the monopolar input cable 140 of the adaptor 130 includes a coagulating current conductive lead 194 connected to the monopolar coagulating current contact pin 148 in the monopolar connector 142 that connects to the coagulating current control output 122 on the face of the RF generator 102. The conductive lead 194 terminates at the adaptor output 152 so that it can conductively connect to a lead 196 in the cable 126b. The monopolar current control switch 128 is conductively connected to the conductive lead 196 through the female pin connector 129a on the cable.

Figure 15A:
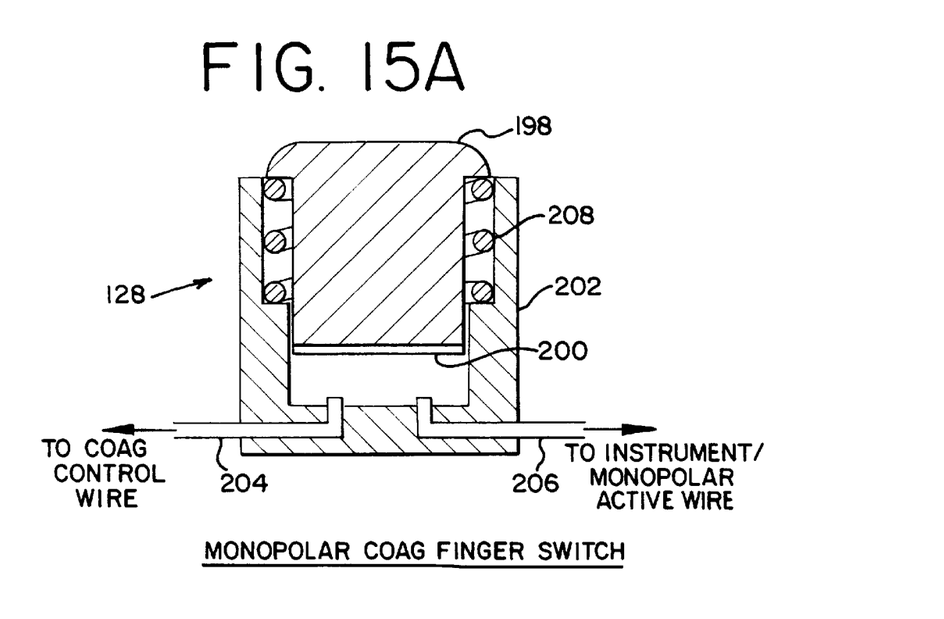
FIG. 15A is a cross-sectional view of a two-position finger switch for use in the present system for activating monopolar coagulating current.

With reference to FIG. 15A, the control switch 128 may comprise a push button 198 having a conductive surface 200 and mounted in a housing 202. A conductive lead 204 connects the switch 128 to the conductive lead 196 in the cable 126b, while a second conductive lead 206 connects the switch 128 to a lead in the instrument that carries monopolar active current to the electrodes. The conductive surface 200 on the push button 198 is biased out of contact with the leads 204, 206 by means of a spring 208. However, when the button 198 is depressed and held so that the conductive surface 200 contacts both the conductive leads 204, 206, the RF generator is activated to generate monopolar coagulating current. Monopolar coagulating current is deactivated when the push button 198 is released.

Alternatively, the control switch 128 can be operable to activate either monopolar coagulating current or monopolar cut current. With reference to FIG. 14, the monopolar input cable 140 of the adaptor 130 includes both a coagulating current conductive lead 194, as described above in conjunction with FIG. 12, and a cut current conductive lead 210 that is connected to the monopolar cut current contact pin 146 of the monopolar connector 142. Both conductive leads 194 and 210 terminate at the adaptor output 152 so that they can conductively connect to leads 196, 212, respectively on the cable 126a. The monopolar current control switch 128 is conductively connected to both conductive leads 196 and 212 at the female pin connector 129a on the cable.

Figure 15B:
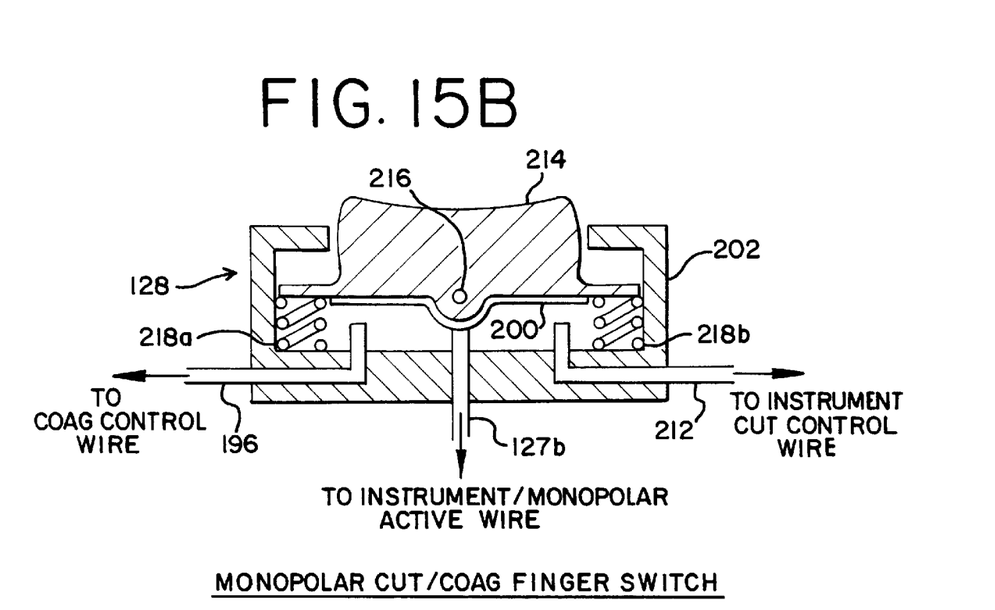
FIG. 15B is a cross-sectional view of a three-position finger switch for use in the present system for activating either monopolar coagulating current or monopolar cut current.

With reference to FIG. 15B the control switch 128 may comprise a double pole rocker switch 214 having a conductive surface 200 and mounted in a housing 202. The conductive surface 200 is connected to a lead in the cable 126a that carries monopolar active current to the electrodes (shown as lead 127b). Both the coagulating current control lead 196 and cut current control lead 212 terminate in the housing 202 and are selectively engageable by the conductive surface 200 by pivoting the rocker switch 214 about a pin 216. Two springs 218a, 218b bias the button 198 to a neutral position. When the button 198 is pivoted and held so that the conductive surface 200 contacts the coagulating control conductive lead 196 and the monopolar active current lead 127b, the RF generator is activated to generate monopolar coagulating current. When the button 198 is pivoted and held so that the conductive surface 200 contacts both the cut control conductive lead 212 and the monopolar active current lead 127b, the RF generator is activated to generate monopolar cut current. When the button is released, the RF generator is deactivated.

Figure 16:
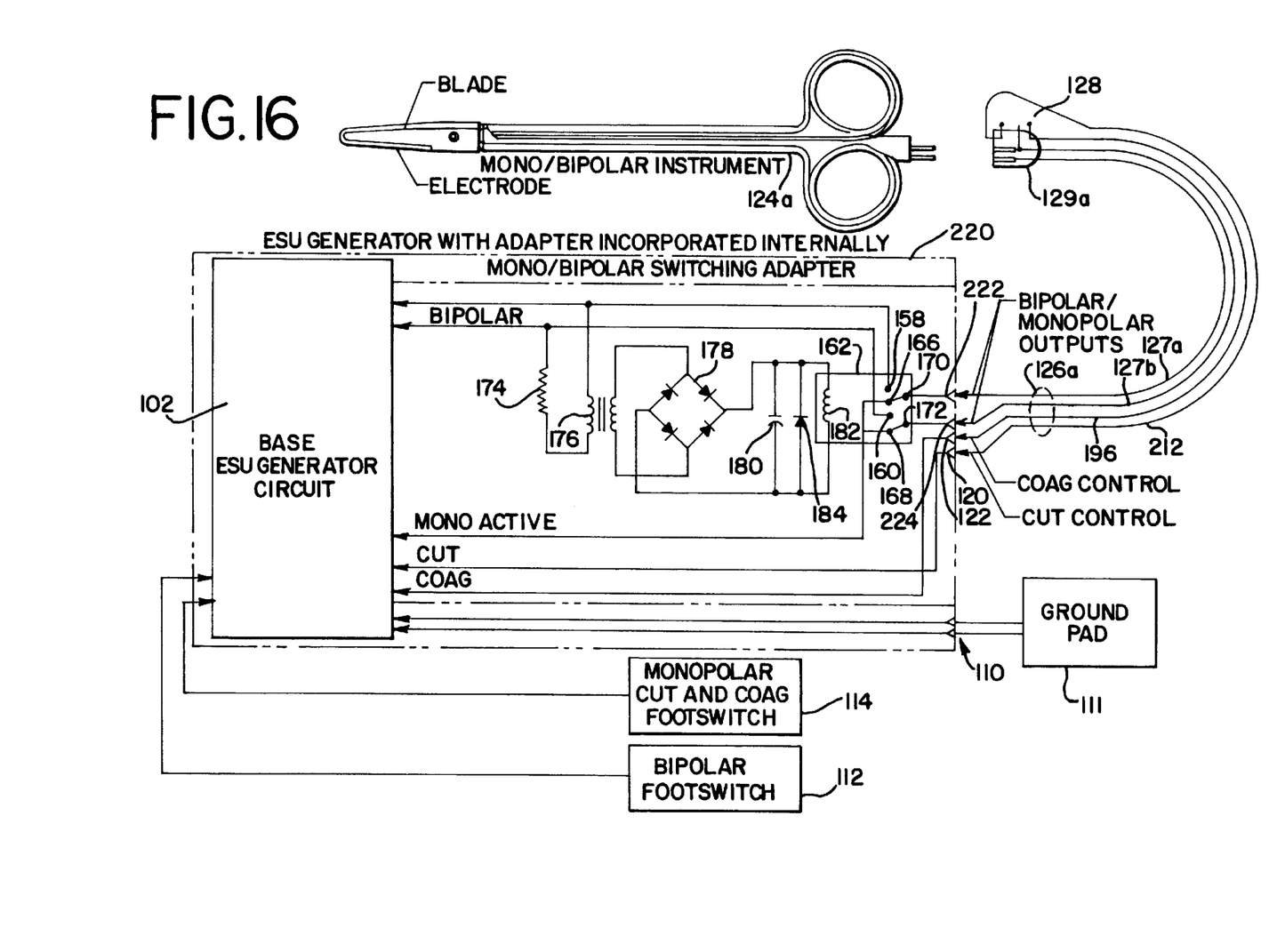
FIG. 16 is a diagrammatic representation of an electrosurgical instrument system similar to that shown in FIG. 14, except that the switching circuit and RF generator share a common housing.

While the adapter has been 130 has been illustrated and described as suitable for use with generally available RF generators that provide both monopolar and bipolar RF energy, (such as the Valley Lab Force II RF generator), the circuitry for the adapter can be incorporated into an RF generator itself. For example, in FIG. 16 there is seen an electrosurgical instrument system similar to that shown in FIG. 14 except that this RF generator 102 and automatic switching adapter 130 share a common housing 220. In contrast to FIGS. 11–14, the faceplate of the housing 220 directly receives the proximal end of the instrument cable 126a through combination monopolar/bipolar outputs 222, 224 and the monopolar cut and coagulating current control outputs 120, 122, respectively. The pin connector 110 for the monopolar return is unchanged.

While the invention has been described in the context of certain preferred embodiments, there is no intent to limit the invention to the same. On the contrary, is intended to cover all equivalents coming within the scope of the attached claims.

What is claimed is:

1. An adapter system for connecting an electrosurgical instrument having first and second electrodes to an RF electrosurgery energy generator having a bipolar energy source and a monopolar energy source, said adapter system comprising:

a bipolar conductor for connecting to said bipolar energy source;

a monopolar conductor for connecting to said monopolar energy source; and a controller having a bipolar input for connecting to said bipolar conductor, a monopolar input for connecting to said monopolar conductor, and an output for connecting to the first and/or second electrodes of the electrosurgical instrument, said controller including a switch that is powered by the RF energy received through one of the monopolar and bipolar conductors and being operable to automatically switch said output into communication with selected of said monopolar conductor and bipolar conductor upon detecting activation of said monopolar or bipolar energy sources.

2. The adapter system of claim 1 wherein said bipolar conductor comprises a first bipolar lead for connection to a first bipolar terminal of an RF generator and a second bipolar lead for connection to a second bipolar terminal of an RF generator; said monopolar conductor comprises a first monopolar lead for connection to a monopolar output terminal of an RF generator; and said controller being operable to automatically connect said first and second bipolar leads to said output of said controller upon activation of first and second bipolar terminals of the RF generator.

3. The adapter system of claim 2 wherein said controller further connects said first monopolar lead to said output of said controller upon deactivation of first and second bipolar terminals of the RF generator.

4. The adapter system of claim 2 wherein said controller further comprises a switching circuit having a relay to automatically connect said first and second bipolar leads to said output of said controller upon activation of first and second bipolar terminals of the RF generator.

5. The adapter system of claim 4 wherein said controller further connects said first monopolar lead to said output of said controller upon deactivation of first and second bipolar terminals of the RF generator.

6. The adapter system of claim 4 wherein said controller further comprises a resistor across which said first and second bipolar leads are connected, a transformer in parallel with said resistor, and a rectifier in parallel with said transformer, the output of said rectifier actuating said relay to conductively connect said bipolar leads to said output of said controller.

7. The adapter system of claim 1 wherein said bipolar conductor comprises a first bipolar lead for connection to a first bipolar terminal of an RF generator and a second bipolar lead for connection to a second bipolar terminal of an RF generator; said monopolar conductor comprises a first monopolar lead for connection to a monopolar output terminal of an RF generator and a second monopolar lead for connection to a monopolar return terminal; and said controller being operable to automatically connect said first monopolar lead to said output of said controller upon activation of the monopolar output terminal of the RF generator.

8. The adapter system of claim 7 wherein said adapter further connects said first and second bipolar leads to said output of said controller upon deactivation of the monopolar output terminal of the RF generator.

9. The adapter system of claim 7 wherein said controller further comprises a switching circuit having a relay to automatically connect said monopolar lead to said output of said controller upon activation of the monopolar output terminal of the RF generator.

10. The adapter system of claim 9 wherein said controller further connects said first and second bipolar leads to said output of said controller upon deactivation of the monopolar output terminal of the RF generator.

11. The adapter system of claim 9 wherein said controller further comprises a resistor connecting said first and second monopolar leads, a transformer in parallel with said resistor, and a rectifier in parallel with said transformer, the output of said rectifier actuating said relay to conductively connect said monopolar leads to said output of said controller.

12. The adapter system of claim 9, 6, or 11 wherein said relay comprises a double pole-double throw relay connected to two common contacts.

13. The adapter system of claim 9, 6, or 11 wherein said controller further comprises a diode connected in parallel with said relay to dissipate current caused by de-energizing said relay.

14. The adaptor system of claim 1 wherein said adaptor is contained within a common housing with the RF electrosurgery energy generator.

15. The adapter system of claim 14 wherein said bipolar conductor comprises a first bipolar lead for connection to a first bipolar output in an RF generator and a second bipolar lead for connection to a second bipolar output in an RF generator; said monopolar conductor comprises a first monopolar lead for connection to a monopolar output in an RF generator and a second monopolar lead for connection to a monopolar return in an RF generator; and said controller being operable to automatically connect said first monopolar lead to said output of said controller upon activation of the monopolar output in the RF generator.

16. The adapter system of claim 15 wherein said adapter further connects said first and second bipolar leads to said output of said controller upon deactivation of the monopolar output in the RF generator.

17. The adaptor system of claim 1 wherein said adaptor is separate from a housing for the RF electrosurgery generator.

18. The adapter system of claim 17 wherein said bipolar conductor comprises a first bipolar lead for connection to a first bipolar output in an RF generator and a second bipolar lead for connection to a second bipolar output in an RF generator; said monopolar conductor comprises a first monopolar lead for connection to a monopolar output in an RF generator; and said controller being operable to automatically connect said first and second bipolar leads to said output of said controller upon activation of first and second bipolar terminals of the RF generator.

19. The adapter system of claim 18 wherein said adapter further connects said first monopolar lead to said output of said controller upon deactivation of first and second bipolar terminals of the RF generator.

20. The adaptor system of claim 1 wherein said controller disconnects said bipolar conductor from said output before connecting said monopolar conductor to said output.

21. The adapter system of claim 20 wherein said controller further disconnects said monopolar conductor from said output before connecting said bipolar conductor to said output.

22. An electrosurgical instrument system comprising:
an RF energy source including a bipolar energy source, and a monopolar energy source, a switch for energizing said bipolar energy source, and a switch for energizing said monopolar energy source;
an electrosurgical instrument having first and second tissue contacting members, a selected of said first and second tissue contacting members comprising a first electrode, a selected of said first and second tissue contacting members comprising a second electrode; and
an adapter for conductively connecting said first and second electrodes to a selected of said bipolar and monopolar energy sources, said adapter comprising:
a bipolar conductor for connecting to said bipolar energy source;
a monopolar conductor for connecting to said monopolar energy source; and
a controller having a bipolar input for connecting to said bipolar conductor, a monopolar input for connecting to said monopolar conductor, and an output for connecting to the first and/or second electrodes of the electrosurgical instrument, said controller including a switch that is powered by the RF energy received through one of the monopolar and bipolar conductors and being operable to automatically switch said output into communication with selected of said monopolar conductor and bipolar conductor upon detecting activation of said monopolar or bipolar energy source.

23. The electrosurgical instrument system of claim 22 wherein said bipolar energy source comprises a first bipolar terminal and a second bipolar terminal, said monopolar energy source comprises a monopolar output terminal; said bipolar conductor comprises a first bipolar lead for connecting to said first bipolar terminal and a second bipolar lead for connecting to said second bipolar terminal; said monopolar conductor comprises a first monopolar lead for connecting to said monopolar output terminal; and said controller being operable to automatically connect said first and second bipolar leads to said output of said controller upon activation of bipolar energy from the RF generator.

24. The electrosurgical instrument system of claim 23 wherein said controller further connects said first monopolar lead to said output of said controller upon deactivation of bipolar energy from the RF generator.

25. The electrosurgical instrument system of claim 23 wherein said controller further comprises a switching circuit having a relay to automatically connect said first and second bipolar leads to said output of said controller upon activation of bipolar energy from the RF generator.

26. The electrosurgical instrument system of claim 25 wherein said switching circuit further connects said first monopolar lead to said output of said controller upon deactivation of bipolar energy from the RF generator.

27. The electrosurgical instrument system of claim 25 wherein said controller further comprises a resistor across which said first and second bipolar leads are connected, a transformer in parallel with said resistor, and a rectifier in parallel with said transformer, the output of said rectifier actuating said relay to conductively connect said bipolar leads to said output of said controller.

28. The electrosurgical instrument system of claim 22 wherein said bipolar energy source comprises a first bipolar terminal and a second bipolar terminal, said monopolar energy source comprises a monopolar output terminal and a monopolar return terminal; said bipolar conductor comprises a first bipolar lead for connecting to said first bipolar terminal and a second bipolar lead for connecting to said second bipolar terminal; said monopolar conductor comprises a first monopolar lead for connecting to said monopolar output terminal and a second monopolar lead for connecting to said monopolar return terminal; and said controller being operable to automatically connect said first monopolar lead to said output of said controller upon activation of monopolar energy from the RF generator.

29. The electrosurgical instrument system of claim 28 wherein said controller further connects said first and second bipolar leads to said output of said controller upon deactivation of monopolar energy from the RF generator.

30. The electrosurgical instrument system of claim 28 wherein said controller further comprises a switching circuit having a relay to automatically connect said first monopolar lead to said output of said controller upon activation of monopolar energy from the RF generator.

31. The electrosurgical instrument system of claim 30 wherein said switching circuit further connects said first and second bipolar leads to said output of said controller upon deactivation of monopolar energy from the RF generator.

32. The electrosurgical instrument system of claim 30 wherein said controller further comprises a resistor connecting said first and second monopolar leads, a transformer in parallel with said resistor, and a rectifier in parallel with said transformer, the output of said rectifier actuating said relay to conductively connect said monopolar leads to said output of said controller.

33. The electrosurgical instrument system of claim 30, 27, or 32 wherein said relay comprises a double pole, double throw relay connected to two common contacts selected of said first and second bipolar leads or said first monopolar lead.

34. The electrosurgical instrument system of claim 30, 27, or 32 wherein said controller further comprises a diode connected in parallel with said relay to dissipate current caused by de-energizing said relay.

35. The electrosurgical instrument system of claim 22 wherein said electrosurgical energy source includes a monopolar control lead, a conductor connected to said control lead, and a control switch interposed between said conductor and said first monopolar output lead for manually activating monopolar energy.

36. The electrosurgical instrument system of claim 35 wherein said control switch is located on said electrosurgical instrument.

37. The electrosurgical instrument system of claim 35 wherein said control switch is located on a conductive lead connecting said adapter to said electrosurgical instrument.

38. The electrosurgical instrument system of claim 35, 36, or 37 wherein said monopolar control lead comprises a coagulation control lead and said control switch comprises a coagulation control switch for manually activating monopolar coagulation energy.

39. The electrosurgical instrument system of claim 38 wherein said electrosurgical energy source further comprises a monopolar cut control lead, a conductor connected to said cut control lead, and a cut control switch interposed between said cut conductor and said first monopolar output lead for manually activating monopolar cut energy.

40. The electrosurgical instrument system of claim 39 wherein said cut control switch is located on said electrosurgical instrument.

41. The combination of claim 39 or 40 wherein said coagulation control switch and said cut control switch comprise a single three position switch.

42. The combination of claim 41 wherein said three position switch comprises a double pole rocker switch.

43. The electrosurgical instrument system of claim 22 wherein said adaptor is contained within a common housing with said RF energy source.

44. The electrosurgical instrument system of claim 22 wherein said adaptor is separate from a housing for said RF energy source.

45. The electrosurgical instrument system of claim 22 wherein said controller disconnects said bipolar conductor from said output before connecting said monopolar conductor to said output.

46. The electrosurgical instrument system of claim 45 wherein said controller further disconnects said monopolar conductor from said output before connecting said bipolar conductor to said output.

* * * * *